United States Patent [19]

Raeymaekers et al.

[11] Patent Number: 4,826,862

[45] Date of Patent: May 2, 1989

[54] ANTHELMINTHIC [(5(6) (1H-AZOLE-1-YLMETHYL)BENZIMIDAZOLE]CARBAMATES

[75] Inventors: Alfons H. M. Raeymaekers, Beerse; Eddy J. E. Freyne, Rumst, both of Belgium

[73] Assignee: Janssen Pharmaceutica, N.V., Beerse, Belgium

[21] Appl. No.: 155,464

[22] Filed: Feb. 12, 1988

[51] Int. Cl.[4] .................... A01N 43/52; C07D 403/06
[52] U.S. Cl. .................... 514/388; 514/383; 548/262; 548/306
[58] Field of Search ........... 548/306, 262; 514/383, 514/388

[56] References Cited

U.S. PATENT DOCUMENTS

| | | | |
|---|---|---|---|
| 3,935,209 | 1/1976 | Beard et al. | 548/306 X |
| 3,969,526 | 7/1976 | Gyvrik et al. | 548/306 X |
| 4,512,998 | 4/1985 | Nafissi-Varchei | 548/306 X |

*Primary Examiner*—Richard A. Schwartz

[57] ABSTRACT

Novel [(5(6) (1H-azole-1-ylmethyl)benzimidazole]carbamates derivatives having anthelminthic properties, compositions containing these compounds as active ingredient, and a method for combating the growth of helminths.

9 Claims, No Drawings

ANTHELMINTHIC [(5(6)(1H-AZOLE-1-YLMETHYL)BENZIMIDAZOLE]-CARBAMATES

BACKGROUND OF THE INVENTION

A large number of benzimidazole carbamates have been described as anthelminthics. As most successful representatives their may be named mebendazole and flubendazole both described in U.S. Pat. No. 3,657,267, albendazole and oxibendazole described in U.S. Pat. No. 3,682,952 and fenbendazole described in German Pat. No. 21,64,690.

The benzimidazole carbamates of the present invention differ therefrom by the fact that they contain a benzimidazole moiety which is invariably substituted in the 5(6) position with a 1H-azol-1-ylmethyl radical and by their favourable anthelminthic spectrum.

DESCRIPTION OF THE PREFERRED EMBODIMENT

The present invention is concerned with novel benzimidazole carbamates of formula

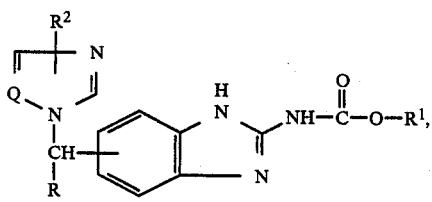

the pharmaceutically acceptable acid addition salts and the stereochemically isomeric forms thereof, wherein R is $C_1$–$C_6$alkyl, $C_{3-6}$cycloalkyl, thienyl or phenyl optionally substituted with up to 3 substituents each independently selected from the group consisting of halo, $C_1$–$C_6$alkyl and $C_1$–$C_6$alkyloxy;

$R^1$ is $C_1$–$C_6$alkyl;

$R^2$ is hydrogen or $C_1$–$C_6$alkyl; and

Q is N or CH.

As used in the foregoing definitions the term halo is generic to fluoro, chloro, bromo and iodo; and the term "$C_1$–$C_6$alkyl" is meant to include straight and branch chained saturated hydrocarbon radicals having from 1 to 6 carbon atoms such as, for example, methyl, ethyl, propyl, 1-methylethyl, 1,1-dimethylethyl, 2-methylpropyl, butyl, pentyl, hexyl and the like; $C_3$–$C_7$cycloalkyl defines cyclopropyl, cyclobutyl, cyclopentyl and cyclohexyl.

It is to be understood that the 1H-azole-1-ylmethyl moiety is substituted on either the 5 or 6 position of the benzimidazole ring. Also within the scope of the invention are the compounds of formula (I) in the form of hydrates or in solvent addition forms.

Preferred compounds within the present invention are those compounds of formula (I) wherein $R^1$ is methyl or ethyl and $R^2$ is hydrogen.

Particularly preferred compounds within the present invention are those preferred compounds of formula (I) wherein Q is CH and R is phenyl or 4-halophenyl.

The compounds of formula (I) can generally be prepared by N-alkylating a 1H-azole of formula (III) with a benzimidazole carbamate of formula (II) or an acid addition salt thereof.

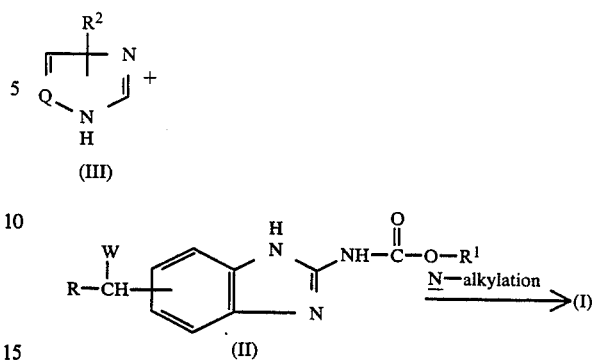

W as used in the foregoing and following reaction schemes is an appropriate leaving group such as, for example, halo, e.g., chloro, bromo or iodo, or a sulfonyloxy group, e.g., a methylsulfonyloxy or 4-methylphenylsulfonyloxy group.

The above described N-alkylation is conveniently carried out by stirring the reactants in the presence of a suitable organic solvent such as, for example, an aromatic hydrocarbon, e.g., benzene, methylbenzene, dimethylbenzene, and the like; a ketone, e.g., 2-propanone, 4-methyl-2-pentanone and the like; an ether, e.g., 1,4-dioxane, 1,1'-oxybisethane, tetrahydrofuran and the like; a polar aprotic solvent, e.g., N,N-dimethylformamide (DMF), N,N-dimethylacetamide (DMA), nitrobenzene, dimethyl sulfoxide (DMSO), 1,3-dimethyl-3,4,5,6-tetrahydro-2(1H)-pyrimidinone (DMPU), 1,3-dimethyl-2-imidazolidinone (DMEU), 1-methyl-2-pyrrolidinone, acetonitrile, hexamethylphosphor triamide (HMPT), benzonitrile and the like; and mixture of such solvents. Somewhat elevated temperatures may be appropriate to enhance the rate of the reaction. In order to enhance the reaction rate it may be advantageous to use an excess of azole or to add to the reaction mixture an appropriate base such as, for example, an alkali metal carbonate or hydrogen carbonate, sodium hydride or an organic base such as, for example, N,N-diethylethanamine, 1,8-diazabicylo[5.4.0]undec-7-ene, N-(1-methylethyl)-2-propanamine and the like.

In some cases it may be advantageous to first convert the 1H-azole of formula (III) to its alkali metal salt form. The said salt form can conveniently be prepared by reacting 1H-azole (III) with an alkali metal base such as, for example, an alkali metal hydroxide, alkoxide or hydride.

Compounds of formula (I) may also be prepared by reacting an alcohol of formula (IV) with a 1,1'-carbonylbis[1H-azole] of formula (V), e.g., a 1,1'-carbonylbis[1H-imidazole].

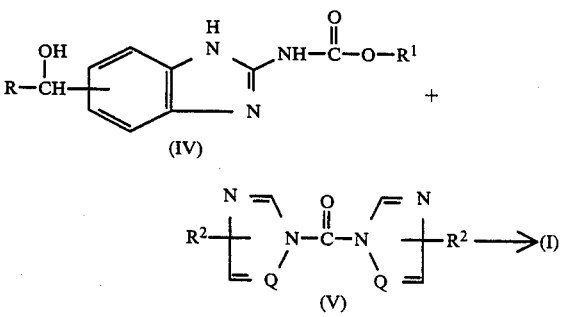

Said reaction may conveniently be conducted in a suitable solvent such as, for example, an ether, e.g., 1,4-dioxane, tetrahydrofuran; a halogenated hydrocarbon, e.g., di- or trichloromethane; a hydrocarbon, e.g., benzene, methylbenzene; a ketone, e.g., 2-propanone, 4-methyl-2-pentanone, N,N-dimethylformamide, N,N-dimethylacetamide, or mixtures of such solvents. In order to enhance the reaction rate, it may be advantageous to heat the reaction mixture, preferably to the reflux temperature of the reaction mixture.

The compounds of formula (I) can also be prepared by ring closure of an appropriately substituted benzenediamine of formula (VI) or an acid addition salt thereof, with an appropriate urea or isothiourea derivative of formula (VII).

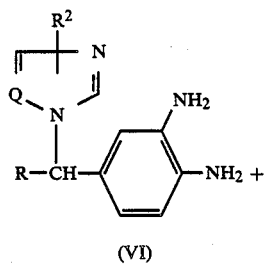

(VI)

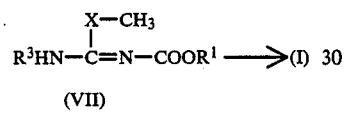

(VII)

In the formulae (VI) and (VII) the symbols R, $R^1$, $R^2$ and Q have the same meanings as previously defined, whereas X is S or O and $R^3$ is hydrogen or a radical of formula $-COOR^1$.

Without being bound by any theory, it is assumed that the intermediates of formula (VII) may occur in tautomeric forms as tentatively illustrated in the following scheme.

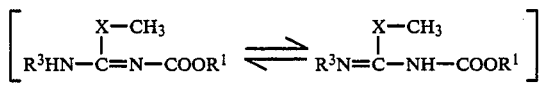

Such tautomeric forms are naturally intented to be within the meaning of formula (VII).

The cyclization of (VI) with (VII) can conveniently be carried out by stirring the reactants in a suitable solvent in the presence of an appropriate acid, such as, for example, a carboxylic acid, e.g. formic, acetic or propionic acid. Somewhat elevated temperatures may be appropriate in order to enhance the rate of the reaction and most preferably the reaction is carried out at the reflux temperature of the reaction mixture. In certain instances it may be advantageous to carry out the reaction under pressure. Suitable solvents comprise organic solvents such as, for example, lower alkanols, e.g., methanol, ethanol, 2-propanol and the like alcohols; aromatic hydrocarbons, e.g., benzene, methylbenzene, chlorobenzene and the like; halogenated hydrocarbons, e.g., trichloromethane, dichloromethane, trichloroethane, trichloroethylene and the like; nitriles such as, for example, acetonitrile; and other common polar aprotic solvents such as, dimethylformamide and the like. Mixtures of such solvents with water may also be employed, e.g., mixtures of water with lower alkanols.

Benzimidazole carbamates of formula (I) may also be prepared by reacting a diamine of formula (VI) or an acid addition salt thereof with a cyanocarbamate of formula (VIII).

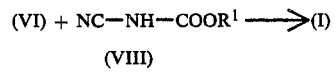

(VIII)

Said reaction may be effected following art-known procedures as described, for example, in U.S. Pat. No. 3,682,952, by reacting (VI) with a cyanocarbamate of formula (VIII) which may be formed in situ by reacting cyanamide with an appropriate haloformate ester in a suitable solvent such as pyridine or if appropriate in water; a lower alkanol, e.g., methanol, ethanol; a ketone, e.g., 2-propanone; a polar aprotic solvent, e.g., N,N-dimethylformamide, N,N-dimethylacetamide, dimethyl sulfoxide; or mixtures of such solvents, preferably in the presence of an appropriate base such as, for example, an alkali metal carbonate or hydroxide. Somewhat elevated temperatures may enhance the rate of the reaction.

Alternatively, the benzimidazole carbamates of formula (I) may be prepared by reacting a benzenediamine of formula (VI) with cyanogen bromide and reacting the thus obtained 2-aminobenzimidazole with an appropriate haloformate ester, e.g., chloroformate ester.

The compounds of formula (I) may alternatively be prepared under similar procedures as are described in the literature for the preparation of related benzimidazole carbamates starting from appropriately substituted benzenediamines. A number of such procedures are described, for example, in "The chemistry of Heterocyclic Compounds" Vol. 40, part 1, pages 1–60, J. Wiley & Sons, New York (1981) and the references cited therein.

In all of the foregoing and in the following preparations, the reaction products may be isolated from the reaction mixture and, if necessary, further purified according to methodologies generally known in the art.

The compounds of formula (I) may also be converted into each other following art-known functional group transformation procedures.

The compounds of formula (I) may be converted to their therapeutically active non-toxic acid addition salt forms by treatment with appropriate acids, such as, for example, inorganic acids, such as hydrohalic acid, e.g., hydrochloric, hydrobromic and the like, and sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

Some intermediates and starting materials in the foregoing preparations are known compounds which may be prepared according to art-known methodologies of preparing said or similar compounds and others are new. A number of such preparation methods will be described hereinafter in more detail.

The intermediates of formula (II) wherein W represents an appropriate leaving group can be obtained by converting an alcohol of formula (IV) into a leaving group following standard procedures as known in the art.

Halides are generally prepared by the reaction of (IV) with an appropriate halogenating agent such as, for example, thionyl chloride, sulfuryl chloride, pentachlorophoshorane, hydrogen bromide, pentabromophoshorane, phosphoryl chloride and the like. When the leaving group is a iodide it is preferably prepared from the corresponding chloride or bromide by the replacement of that halogen with iodine. Other leaving groups such as methanesulfonates and 4-methylbenzenesulfonates may be obtained by the reaction of the alcohol with an appropriate sulfonyl halide such as, for example, methanesulfonyl chloride or 4-methylbenzenesulfonyl chloride respectively.

The benzenediamines of formula (VI) may be prepared from an appropriately substituted ketone of formula (IX) according to the following reaction sequence.

A ketone of formula (IX) is reduced with an appropriate reductant, e.g., sodium borohydride in a suitable solvent, e.g., methanol and subsequently reacted with a 1,1′-carbonylbis[1H-azole] of formula (V) following the same procedures as described hereinabove for the preparation of (I) starting from (IV) and (V). The nitro function in the thus obtained intermediate (XI) is then subjected to a nitro-to-amine reduction reaction by stirring the former in a hydrogen containing medium in the presence of a suitable amount of a catalyst such as, for example, platinum-on-charcoal, palladium-on-charcoal, Raney-nickel and the like.

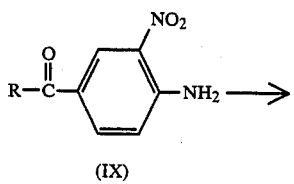

(IX)

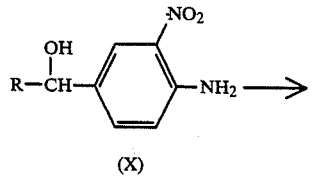

(X)

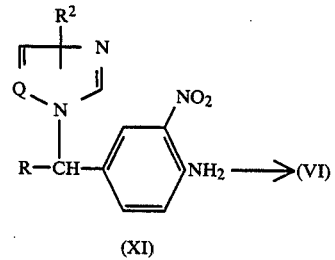

(XI)

Starting materials and intermediates for which no specific preparations are given herein, are generally known and/or may all be prepared following art-known methodologies described in the literature for the preparation of similar known compounds.

All references cited hereinabove are incorporated herein as reference.

The compounds of formula (I) and some of the intermediates in this invention have at least one asymmetric carbon atom in their structure. This chiral center may be present in a R- and a S-configuration, this R- and S-notation being in correspondence with the rules described in J. Org. Chem., 35, 2849–2867 (1970).

Pure stereochemically isomeric forms of the compounds of this invention may be obtained by the application of art known procedures. Diastereoisomers may be separated by physical separation methods such as selective crystallization and chromatographic techniques, e.g., counter current distribution, and enantiomers may be separated from each other by the selective crystallization of their diastereomeric salts with optically active acids, or the like methods.

Pure stereochemically isomeric forms may also be derived from the corresponding pure stereochemically isomeric forms of the appropriate starting materials, provided that the reaction occurs stereospecifically.

Stereochemically isomeric forms of the compounds of formula (I) are naturally intended to be embraced within the scope of the invention.

The compounds of formula (I), the pharmaceutically acceptable acid-addition salts and stereochemically isomeric forms thereof have anthelminthic properties, in particular they possess a broad spectrum activity against parasites of warm blooded animals (human or animal), including both mature and immature parasitic forms, as represented for example by Nematodes, such as, *Syngamus trachea* in turkeys and pheasants, Ascaridia and Heterakis in chickens, *Toxocara cati* in cats, *Ankylostoma tubaeforme* in cats, *Toxocara canis* in dogs, *Toxascaris leonina* in dogs, *Uncinaria stenocephala* in dogs, *Ankylostoma cannium* in dogs, *Trichuris vulpis* in dogs, *Trichinella spiralis* in pigs and rats, *Dictyocaulus filaria* in sheeps and Trichostrongyliden in sheeps; and in particular, Cestodes, such as, *Hymenolepsis diminuta* in rats, *Taenia pisiformis* in dogs, *Taenia hydatigena* in dogs, *Taenia ovis* in dogs, *Dipylidium cannium* in dogs, *Taenia taeniaeformis* in cats, Moniezia in sheeps, Anitellina sp in sheeps, Raillietina, *Hydatigera taeniaformis* and the like. In particular, the compounds of the invention are found to exhibit high activity against various helminthic infections of the intestinal tract of man and economically important animals, such as, sheeps, cattles, horses, pigs and poultry coupled with low systemic toxicity to the host.

The anthelminthic properties of compounds of formula (I) can be demonstrated for example in the "*Hymenolepsis diminuta* in artificially infected rats"-test and the "*Taenia pisiformis* in artificially infected dogs"-test illustrating useful anthelminthic properties of the compounds of the present invention.

In view of their useful anthelminthic properties the subject compounds may be formulated into various pharmaceutical forms for administration purposes. To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as a pour on, as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In the instance where economically important animals are raised in large numbers, particularly poultry and birds, it is advantageous to add the compounds of formula (I) directly to the feed, as such, or in the form of a premix or concentrate. In addition, the compounds of formula (I) may also be administered while dissolved or suspended in the drinking water.

In view of the anthelminthic properties of the compounds of formula (I) it is evident that the present invention provides anthelminthic compositions comprising an anthelminthically effective amount of an active compound of formula (I), either alone or in admixture with other active therapeutic ingredients such as, closantel, in admixture with suitable carriers.

In view of their potent activity in combatting helminthis the compounds of this invention constituted useful tools for the destruction or prevention of the growth of the helminthis and more particularly they can effectively be used in the treatment of subjects suffering from such helminthis. Therefore the present invention provides a method of destructing or preventing the growth of helminthis in warm blooded animals suffering from such helminthis by administration of an anthelminthically effective amount of a compound of formula (I), a pharmaceutically acceptable acid addition salt or a possible stereochemically isomeric form thereof.

Those of skill in treating warm blooded animals suffering from such parasites could easily determine the effective amount from the test results presented herein. In general it is contemplated that an effective amount would be from 1 to 100 body weight, more particularly between 2.5 to 25.0 mg/kg body weight, preferably in a single administration.

The following examples are intended to illustrate and not to limit the scope of the present invention. Unless otherwise stated all parts therein by weight.

EXPERIMENTAL PART

A. Preparation of Intermediates

Example 1

(a) A mixture of 9.6 parts of methyl [5-(6)-(4-fluorophenyl)-1$\underline{H}$-benzimidazol-2-yl]carbamate, 3 parts of sodium tetrahydroborate, 96 parts of methanol, 30 parts of water and 15 parts of a sodium hydroxide solution 2N was stirred for 48 hours at 30°~35° C. The precipitated product was filtered off and washed with 2-propanone. After drying at 50° C., the product was stirred in water, previously acidified with acetic acid. It was filtered off and dried at 60° C., yielding 3.2 parts of methyl [5-[(4-fluorophenyl)hydroxymethyl]-1$\underline{H}$-benzimidazol-2-yl]carbamate; mp. 300° C.; (int. $\overline{1}$).

(b) A solution of 6.3 parts of methyl [5-[(4-fluorophenyl)hydroxymethyl]-1$\underline{H}$-benzimidazol-2-yl]carbamate in 60 parts of acetic acid, saturated with hydrogen bromide was stirred for 3 hours at room temperature. The reaction mixture was evaporated, yielding 9.18 parts (99.9%) of methyl [5-[bromo(4-fluorophenyl)methyl]-1$\underline{H}$-benzimidazol-2-yl]carbamate monohydrobromide as a residue (int. 2).

Example 2

(a) To a stirred solution of 20 parts of (4-amino-3-nitrophenyl)(4-fluorophenyl)methanone in 120 parts of methanol were added 3.8 parts of sodium tetrahydroborate. The whole was stirred for 30 minutes at room temperature. 12 Parts of acetic acid were added and the mixture was stirred for 15 minutes. After evaporation, water was added to the residue. The product was extracted with 2,2'-oxybispropane. The extract was dried, filtered and evaporated, yielding 20 parts (99%) of 4-amino-α-(4-fluorophenyl)-3-nitrobenzenemethanol as a residue (int. 3).

(b) To a stirred solution of 20 parts of 4-amino-α-(4-fluorophenyl)-3-nitrobenzenemethanol, 0.1 parts of a sodium hydride dispersion 50% and 135 parts of tetrahydrofuran were added 16 parts of 1,1'-carbonylbis[1$\underline{H}$-imidazole]. The whole was stirred and refluxed for $\overline{2}$ hours. The solvent was removed. Water was added to the residue. The oily layer was separated, dissolved in dichloromethane, dried, filtered and evaporated. The residue was crystallized from a mixture of 65 parts of dichloromethane and 45 parts of benzene. The precipitate was filtered off and the filtrate was evaporated. The residue was purified by column chromatography over silica gel using a mixture of ethyl acetate and methanol (90:10 by volume) as eluent. The pure fractions were collected and the eluent was evaporated. The residue was crystallized from a mixture of 52 parts of dichloromethane and 54 parts of benzene. The product was filtered off and dried, yielding 5.1 parts (21.2%) of 4-[(4-fluorophenyl)(1H-imidazol-1-yl)methyl]-2-nitrobenzenamine; mp. 147,4° C. (int. 4).

(c) A mixture of 6.24 parts of 4-[(4-fluorophenyl)(1H-imidazol-1-yl)methyl]-2-nitrobenzenamine, 1 part of a solution of thiophene in methanol 4% and 200 parts of methanol was hydrogenated at normal pressure and at room temperature with 2 parts of platinum-on-charcoal catalyst 5%. After the calculated amount of hydrogen was taken up, the catalyst was filtered off and the filtrate was evaporated, yielding 5.6 parts of 4-[(4-fluorophenyl)(1H-imidazol-1-yl)methyl]-1,2-benzenediamine as a residue (int. 5).

In a similar manner there were also prepared:
4-[(1H-imidazol-1-yl)phenylmethyl]-1,2-benzenediamine as a residue (int. 6);
4-[(1H-imidazol-1-yl)(2-thienyl)methyl]-1,2-benzenediamine as a residue (int. 7); and
4-[(3-chlorophenyl)(1H-imidazol-1-yl)methyl]-1,2-benzenediamine as a residue (int. 8).

B. Preparation of Final Compounds

Example 3

A solution of 8.3 parts of 4-[(3-chlorophenyl)(1H-imidazol-1-yl)methyl]-1,2-benzenediamine and 4.8 parts of methyl (α-imino-α-methoxymethyl)carbamate in 150 parts of trichloromethane and 10 parts of acetic acid was stirred for 3 days at reflux temperature. After cooling to room temperature, the reaction mixture was poured into crushed ice. The whole was neutralised with ammonium hydroxide. The organic layer was dried, filtered and evaporated. The residue was purified by column chromatography over silica gel using a mixture of dichloromethane and methanol (98:2 by volume) as eluent. The pure fractions were collected and the eluent was evaporated. The residue was crystallized from a mixture of 2-propanone and 1,1'-oxybisethane. The product was filtered off and dried, yielding 2.9 parts (28.7%) of methyl [5-[(3-chlorophenyl)(1H-imidazol-1-yl)methyl]-1H-benzimidazol-2-yl]carbamate; mp. 168.5° C. (compound 1).

In a similar manner there were also prepared:
methyl [5-[(1H-imidazol-1yl)phenylmethyl]-1H-benzimidazol-2-yl]carbamate; mp. 286.0° C. (compound 2);
methyl [5-[(1H-imidazol-1-yl)(2-thienyl)methyl]-1H-benzimidazol-2-yl]carbamate; mp. 194.7° C. (compound 3);
methyl [5-[(4-fluorophenyl)(1H-imidazol-1-yl)methyl]-1H-benzimidazol-2-yl]carbamate; mp. 211.1° C. (compound 4); and
methyl [5-[1-(1H-imidazol-1-yl)butyl]-1H-benzimidazol-2-yl]carbamate; mp. 230.4° C. (compound 5).

Example 4

A mixture of 9.18 parts of methyl [5-[bromo(4-fluorophenyl)methyl]-1H-benzimidazol-2-yl]carbamate monohydrobromide, 12.3 parts of 2-methyl-1H-imidazole and 56.4 parts of N,N-dimethylformamide was stirred for 17 hours at room temperature. The reaction mixture was diluted with 300 parts of water. The precipitated product was filtered off and dissolved in dichloromethane. The organic layer was dried, filtered and evaporated. The residue was purified by column chromatography over silica gel using a mixture of trichloromethane, methanol and methanol, saturated with ammonia, (90:5:5 by volume) as eluent. The pure fractions were collected and the eluent was evaporated. The residue was crystallized from 27 parts of ethyl acetate. The product was filtered off, washed with 1,1'-oxybisethane and dried, yielding 2.6 parts (34.2%) of methyl [5-[(4-fluorophenyl)(2-methyl-1H-imidazol-1-yl)methyl]-1H-benzimidazol-2-yl]carbamate; mp. >300° C. (compound 6).

In a similar manner there were also prepared:
methyl [5-[(4-fluorophenyl)(4-methyl-1H-imidazol-1-yl)methyl]-1H-benzimidazol-2-yl]carbamate; mp. 249.9° C. (compound 7); and
methyl [5-[(4-fluorophenyl)(5-methyl-1H-imidazol-1-yl)methyl]-1H-benzimidazol-2-yl]carbamate; mp. >300° C. (decomp.) (compound 8).

Example 5

To a stirred solution of 11.5 parts of 1H-1,2,4-triazole in 141 parts of N,N-dimethylformamide were added 4.2 parts of a sodium hydride dispersion 50%. After stirring for 30 minutes at room temperature, the mixture was cooled and 13.77 parts of methyl [5-[bromo(4-fluorophenyl)methyl]-1H-benzimidazol-2-yl]carbamate monohydrobromide were added. The reaction mixture was stirred for 3 hours at room temperature. After the addition of 1.8 parts of acetic acid, the N,N-dimethylformamide layer was evaporated in vacuo. The residue was taken up in water. The precipitated product was filtered off, washed with water and 2,2'-oxybispropane and dissolved in dichloromethane. The organic layer was dried, filtered and evaporated. The residue was purified by column chromatography over silica gel using a mixture of trichloromethane and methanol (93:7 by volume) as eluent.

The second fraction was collected and the eluent was evaporated. The residue was further purified by column chromatography over silica gel using a mixture of trichloromethane and methanol (93:7 by volume) as eluent. The pure fractions were collected and the eluent was evaporated. The residue was washed with methanol and dried, yielding 3.1 parts (28.2%) of methyl [5-[(4-fluorophenyl)(1H-1,2,4-triazol-1-yl)methyl]-1H-benzimidazol-2-yl]carbamate; mp. 250.0° C. (compound 9).

Example 6

A mixture of 6 parts of methyl [5-[cyclopropyl(hydroxy)methyl]-1H-benzimidazol-2-yl]carbamate, 4.8 parts of 1,1'-carbonylbis[1H-imidazole] and 178 parts of tetrahydrofuran was stirred for 17 hours at room temperature. The reaction mixture was evaporated. The residue was washed with water and dissolved in trichloromethane. The organic layer was dried, filtered and evaporated. The residue was purified twice by column chromatography over silica gel using a mixture of trichloromethane, methanol and methanol, saturated with ammonia, (90:5:5 by volume) as eluent. The pure fractions were collected and the eluent was evaporated. The residue was crystallized from 72 parts of ethyl acetate. The product was filtered off and dried, yielding 3.2 parts (44.4%) of methyl [5-[cyclopropyl(1H-imidazol-1-yl)methyl]-1H-benzimidazol-2-yl]carbamate; mp. 217.8° C. (compound 10).

C. Biological Examples

The strong anthelminthic activity of the compounds of formula (I) is clearly evidenced by the data obtained in the following experiments, which data are only given to illustrate the useful anthelminthic properties of all the compounds of formula (I) and not to limit the invention either with respect to the scope of susceptible parasites nor with respect to the scope of formula (I).

Example 7

"*Hymenolepis diminuta* in artificially infected Rats"-test

*Hymenolepis diminuta* eggs were collected from the adult tapeworms in rats by maceration of the gravid proglottids on a moisted filter paper. The flour beetle *Tribolium confusum* was bred as an intermediate host for *H. diminuta*. After a six-day-starvation the beetles were put on the filter paper to ingest the tapeworm eggs. Seventeen days after the ingestion, the infected beetles were euthanised and macerated to collect the cysticercoid larvae from the peritoneal cavity.

Young rats were infested orally by gavage with 10 cysticercoids. The larvae develop into adjust worms in about 2 weeks. Before a single treatment with a compound of formula (I), faecal samples were collected from the rats to confirm the infection.

Nine days after the oral administration of a compound of formula (I), the rats were autopsied for worm count. Drug efficacy was calculated by comparing the number of worms in the treated rats with the number of worms in the untreated controls.

For example, compounds Nos. 2 and 4 showed 100% activity after a single treatment of 20 mg/kg.

Example 8

"*Taenia pisiformis* in artificially infected Dogs"-test

Proglottids of *Taenia pisiformis* were collected from the faecal material of the infected dogs.

After maceration and washing in tapewater the eggs were collected by passing the proglottids suspension through a sieve with apperture of 53 micron. The number of eggs were counted and about 1000 eggs were administered by gavage to young rabbits.

After 5 weeks the rabbits had infectious *Cysticercus pisiformis* in th peritoneal cavity. After autopsy of the rabbits the cysticerci were collected and administered orally in a gelatine capsule to young Beagle dogs. The infective dose was about 15 cysticerci.

Two months after the artificial infection the dogs were moved to isolated cages on wire floor to confirm the tapeworms infection by faecal examination.

After a single treatment of these dogs with a compound of formula (I) the faecal material was collected every day for 4 days. Elimination of proglottids and scolices was recorded. Seven days after oral administration of a compound of formula (I) the dogs were autopsied and the efficacy of the compound was determined on the basis of the presence (or absence) of scolices in the intestine.

For example, compound Nos. 3 and 4 showed 100% activity after a single treatment with 2.5 mg/kg.

We claim:

1. A chemical compound of formula

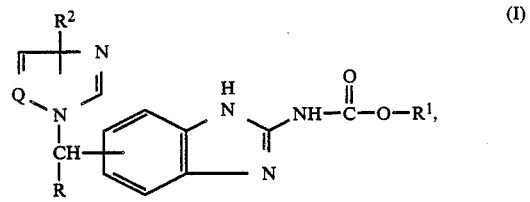

a pharmaceutically acceptable acid addition salt or a stereochemically isomeric form thereof, wherein R is $C_1$-$C_6$alkyl, $C_{3-6}$cycloalkyl, thienyl, phenyl, or phenyl substituted with up to 3 substituents each independently selected from the group consisting of halo, $C_1$-$C_6$alkyl and $C_1$-$C_6$alkyloxy;

$R^1$ is $C_1$-$C_6$alkyl;

$R^2$ is hydrogen or $C_1$-$C_6$alkyl; and

Q is N or CH;

and wherein the 1H-azole-1-ylmethyl moiety is substituted on either the 5 or 6 position of the benzimidazole ring.

2. A chemical compound according to claim 1 wherein $R^1$ is methyl or ethyl and $R^2$ is hydrogen.

3. A chemical compound according to claim 2 wherein Q is CH and R is phenyl or 4-halophenyl.

4. An anthelminthic composition comprising one or more pharmaceutical carriers and as active ingredient and anthelminthic effective amount of at least one compound as claimed in claim 1.

5. An anthelminthic composition comprising one or more pharmaceutical carriers and as active ingredient an anthelminthic effective amount of at least one compound as claimed in claim 2.

6. An anthelminthic composition comprising one or more pharmaceutical carriers and as active ingredient an anthelminthic effective amount of at least one compound as claimed in claim 3.

7. A method of destroying or preventing the growth of helminths in warm-blooded animals suffering from such helminths by the administration of an anthelminthically effective amount of a compound as claimed in claim 1.

8. A method of destroying or preventing the growth of helminths in warm-blooded animals suffering from such helminths by the administration of an anthelminthically effective amount of a compound as claimed in claim 2.

9. A method of destroying or preventing the growth of helminths in warm-blooded animals suffering from such helminths by the administration of an anthelminthically effective amount of a compound as claimed in claim 3.

* * * * *